(12) United States Patent
Ponzi et al.

(10) Patent No.: US 9,433,751 B2
(45) Date of Patent: Sep. 6, 2016

(54) STEERABLE CATHETER WITH DISTAL TIP ORIENTATION SHEATHS

(71) Applicant: BIOSENSE WEBSTER (ISRAEL), LTD., Yokneam (IL)

(72) Inventors: Dean M. Ponzi, Glendora, CA (US); Mario A. Solis, Rancho Cucamonga, CA (US)

(73) Assignee: Biosense Webster (Israel) Ltd. (IL)

( * ) Notice: Subject to any disclaimer, the term of this patent is extended or adjusted under 35 U.S.C. 154(b) by 0 days.

(21) Appl. No.: 13/655,637

(22) Filed: Oct. 19, 2012

(65) Prior Publication Data

US 2013/0046236 A1 Feb. 21, 2013

Related U.S. Application Data

(63) Continuation of application No. 11/132,514, filed on May 19, 2005, now Pat. No. 8,376,990.

(51) Int. Cl.
| | | |
|---|---|---|
| *A61M 31/00* | (2006.01) |
| *A61M 25/01* | (2006.01) |
| *A61B 18/14* | (2006.01) |
| *A61B 17/00* | (2006.01) |
| *A61B 18/00* | (2006.01) |

(52) U.S. Cl.
CPC ...... *A61M 25/0147* (2013.01); *A61B 18/1492* (2013.01); *A61M 25/0144* (2013.01); *A61B 2017/003* (2013.01); *A61B 2018/00577* (2013.01); *A61M 25/0136* (2013.01)

(58) Field of Classification Search
CPC .............. A61M 25/0147; A61M 25/0136; A61M 25/0144
USPC .............. 604/523–532, 95.01–95.05, 96.01, 604/164.01
See application file for complete search history.

(56) References Cited

U.S. PATENT DOCUMENTS

| | | |
|---|---|---|
| 2,498,692 A | 2/1950 | Mains |
| 4,920,980 A | 5/1990 | Jackowski |
| 5,195,968 A | 3/1993 | Lundquist et al. |
| 5,199,950 A | 4/1993 | Schmitt et al. |
| 5,254,088 A | 10/1993 | Lundquist et al. |
| RE34,502 E | 1/1994 | Webster, Jr. |
| 5,318,525 A | 6/1994 | West et al. |
| 5,357,979 A | 10/1994 | Imran |
| 5,395,327 A | 3/1995 | Lundquist et al. |
| 5,456,674 A | 10/1995 | Bos et al. |
| 5,500,012 A | 3/1996 | Brucker et al. |
| 5,507,725 A | 4/1996 | Savage et al. |
| 5,545,200 A | 8/1996 | West et al. |

(Continued)

FOREIGN PATENT DOCUMENTS

| | | |
|---|---|---|
| EP | 0689851 A1 | 1/1996 |
| JP | H05-317429 | 12/1993 |

(Continued)

OTHER PUBLICATIONS

European Search Report dated Jul. 20, 2006 from corresponding European Patent Application No. 06252574.6.

*Primary Examiner* — Phillip Gray

(57) ABSTRACT

A bi-directional electrophysiology catheter having improved steerability which includes orientation sheaths, or thin walled tubes, placed in diametrically opposed lumen at the distal portion of the catheter for producing in-plane deflection of the distal portion of the catheter.

6 Claims, 5 Drawing Sheets

(56) References Cited

U.S. PATENT DOCUMENTS

| | | |
|---|---|---|
| 5,674,197 A | 10/1997 | van Muiden et al. |
| 5,688,266 A | 11/1997 | Edwards et al. |
| 5,688,267 A | 11/1997 | Panescu et al. |
| 5,820,591 A | 10/1998 | Thompson et al. |
| 5,824,031 A | 10/1998 | Cookston et al. |
| 5,906,590 A * | 5/1999 | Hunjan ............ A61M 25/0147 604/264 |
| 6,123,699 A | 9/2000 | Webster, Jr. |
| 6,171,277 B1 | 1/2001 | Ponzi |
| 6,183,463 B1 | 2/2001 | Webster, Jr. |
| 6,198,974 B1 | 3/2001 | Webster, Jr. |
| 6,210,407 B1 | 4/2001 | Webster |
| 6,398,776 B1 | 6/2002 | Sekino et al. |
| 6,522,933 B2 | 2/2003 | Nguyen |
| 6,551,271 B2 | 4/2003 | Nguyen |
| 6,569,114 B2 | 5/2003 | Ponzi et al. |
| 6,571,131 B1 * | 5/2003 | Nguyen ............ A61B 18/1492 607/122 |
| 6,602,242 B1 | 8/2003 | Fung et al. |
| 6,716,166 B2 | 4/2004 | Govari |
| 6,837,867 B2 | 1/2005 | Kortelling |
| 2003/0045831 A1 * | 3/2003 | Ponzi ............ A61M 25/0147 604/95.04 |

FOREIGN PATENT DOCUMENTS

| | | |
|---|---|---|
| JP | H06-292728 | 10/1994 |
| JP | H08-24341 | 11/1994 |
| JP | H10-57500 | 3/1998 |
| JP | 2002-360704 | 12/2002 |
| JP | 2003-153877 | 5/2003 |
| JP | 2003-260057 | 9/2003 |
| WO | WO 96/40344 A1 | 12/1996 |

* cited by examiner

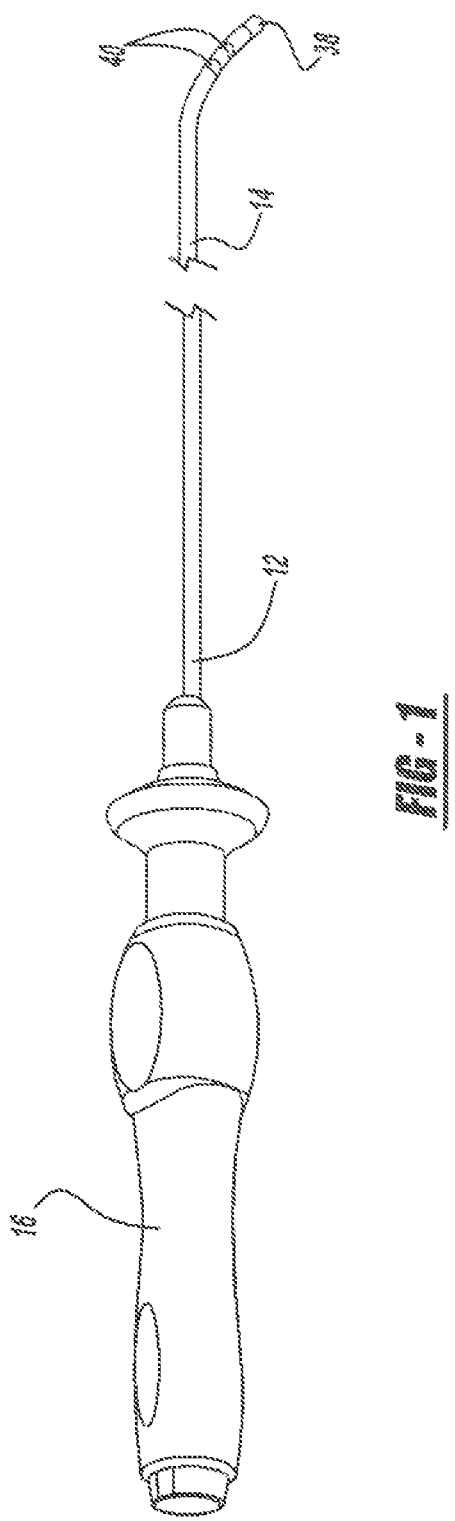

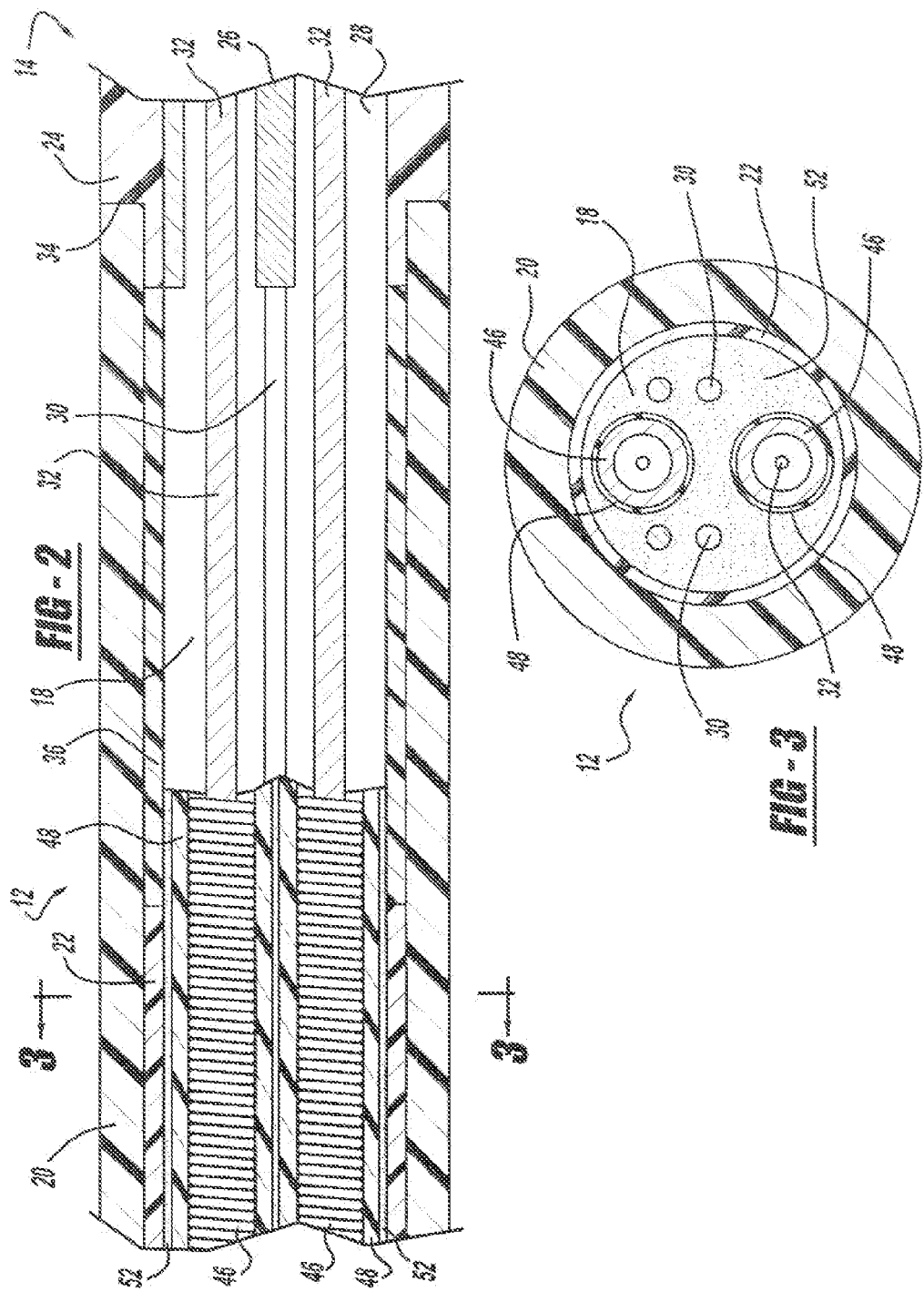

STEERABLE CATHETER WITH DISTAL TIP ORIENTATION SHEATHS

This Application is a Continuation Patent Application of U.S. patent application Ser. No. 11/132,514 filed May 19, 2005.

FIELD OF THE INVENTION

The present invention relates to an improved steerable electrophysiology catheter having a mechanism in the distal tip of the catheter to orient deflection.

BACKGROUND OF THE INVENTION

Electrophysiology catheters have been in common use in medical practice for many years. Such catheters are used to stimulate and map electrical activity in the heart and to ablate sites of aberrant electrical activity.

In use, the electrophysiology catheter is inserted into a major vein or artery, e.g., femoral artery, and then guided into the chamber of the heart which is of concern. Within the heart, the ability to control the exact position and orientation of the catheter tip is critical and largely determines how useful the catheter is.

Steerable (or deflectable) electrophysiology catheters are generally well known. For example, U.S. Pat. No. Re. 34,502 describes a catheter having a control handle comprising a housing having a piston chamber at its distal end. A piston is mounted in the piston chamber and is afforded lengthwise movement. The proximal end of the catheter body is attached to the piston. A puller wire is attached to the housing and extends through the piston and through the catheter body. The distal end of the puller wire is anchored in the tip section of the catheter. In this arrangement, lengthwise movement of the piston relative to the housing results in deflection of the catheter tip section.

Often it is desirable to have a bidirectional steerable catheter, i.e., a catheter that can be deflected in two directions, typically opposing directions. For example, U.S. Pat. No. 6,210,407 discloses a bidirectional steerable catheter having two puller wires extending through the catheter. The distal ends of the puller wires are anchored to opposite sides of the tip section of the catheter. A suitable bidirectional control handle is provided that permits longitudinal movement of each puller wire to thereby allow deflection of the catheter in two opposing directions.

Regardless of whether the catheter is unidirectional or bidirectional, it is typically preferred that the tip section can be deflected in the plane of the catheter so that the catheter can be more precisely controlled in the heart. However, because the tip section is generally made of a flexible material, it is sometimes difficult to limit out-of-plane deflection. Accordingly, a need exists for a catheter having a tip section that can be consistently deflected within a single plane of the catheter.

SUMMARY OF THE INVENTION

The present invention is directed to an improved electrophysiology steerable catheter having orientation sheaths, or tubes, extending through the distal end to improve deflection. More particularly, the catheter includes an elongated, flexible tubular catheter body having proximal and distal ends and a lumen extending therethrough. A tip section is provided at the distal end of the catheter body. The tip section includes flexible plastic tubing having first and second pairs of diametrically opposed lumens extending therethrough. The first pair of diametrically opposed lumens are generally perpendicular to the second pair of diametrically opposed lumens. A control handle is mounted at the proximal end of the catheter body. The catheter further includes first and second puller wires, each extending through one of the lumens of the first pair of diametrically opposed lumens and through the lumen of the catheter body. The puller wires each have a proximal end anchored to the control handle and a distal end anchored to the tip section. The first puller wire is longitudinally moveable relative to the catheter body to cause deflection of the tip section in a plane in a first direction, and the second puller wire is longitudinally moveable relative to the catheter body to cause deflection of the tip section in a plane in a second direction opposite the first direction. The catheter further comprises first and second orientation sheaths, or tubes, each having proximal and distal ends. Each orientation sheath extends through one of the lumens of the second pair of diametrically opposed lumens. The distal end of each orientation sheath is fixedly attached to the wall of the respective lumen at or near the distal end of the tip section, and the proximal end of each orientation sheath is fixedly attached to the wall of the respective lumen at a more proximal portion of the respective lumen.

DESCRIPTION OF THE DRAWINGS

These and other features of the advantages of the present invention will be better understood by reference to the following detailed description when considered in conjunction with the accompanying drawings wherein:

FIG. 1 is a side view of an embodiment of the catheter of the invention.

FIG. 2 is a side cross-sectional view of the junction of the catheter body and tip section of an embodiment of a catheter according to the invention.

FIG. 3 is a transverse cross-sectional view of the catheter body shown in FIG. 2 taken along line 3-3.

DETAILED DESCRIPTION

Figure 4:
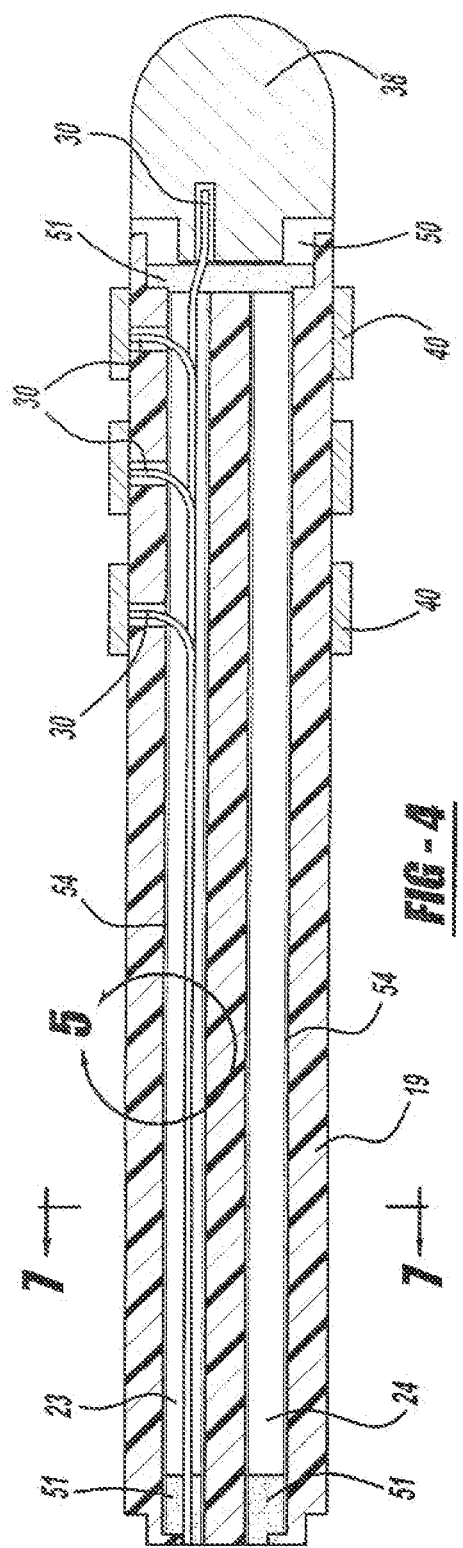
FIG. 4 is a side cross-sectional view of the tip section of the catheter of the invention showing the lumens through which the orientation sheaths and electrode lead wires extend.

In a particularly preferred embodiment of the invention, there is provided a steerable bidirectional electrode catheter. As shown in FIG. 1, the catheter 10 comprises an elongated catheter body 12 having proximal and distal ends, a tip section 14 at the distal end of the catheter body 12, and a control handle 16 at the proximal end of the catheter body 12.

As shown in FIGS. 2 and 3, the catheter body 12 comprises an elongated tubular construction having a single axial or central lumen 18. The catheter body 12 is flexible, i.e., bendable, but substantially non-compressible along its length. The catheter body 12 can be of any suitable construction and made of any suitable material. A presently preferred construction comprises an outer wall 20 made of polyurethane or PEBAX. The outer wall 20 preferably comprises an imbedded braided mesh of stainless steel or the like to increase torsional stiffness of the catheter body 12 so that when the control handle 16 is rotated the tip section 14 will rotate in a corresponding manner.

The overall length and diameter of the catheter 10 may vary according to the application. A presently preferred catheter 10 has an overall length of about 48 inches. The outer diameter of the catheter body 12 is not critical, but is preferably no more than about 8 french. The inner surface of the outer wall 20 is preferably lined with a stiffening tube 22, which can be made of any suitable material, preferably nylon or polyimide. The stiffening tube 22, along with the braided outer wall 20, provides improved flexural and torsional stability while at the same time minimizing the wall thickness of the catheter body 12, thus maximizing the diameter of the central lumen 18. The outer diameter of the stiffening tube 22 is about the same as or slightly smaller than the inner diameter of the outer wall 20. A particularly preferred catheter 10 has an outer diameter of about 0.092 inch and a lumen 18 diameter of about 0.052 inch. If desired, the stiffening tube can be omitted.

Figure 5:
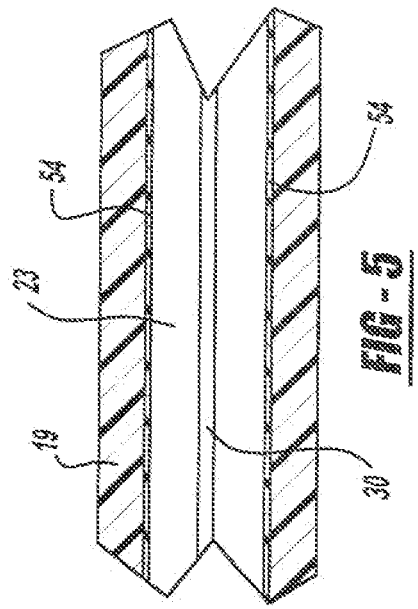
FIG. 5 is a side cross-sectional view of the tip section of the catheter of the invention showing the lumens through which the pullers extend.
Figure 6:
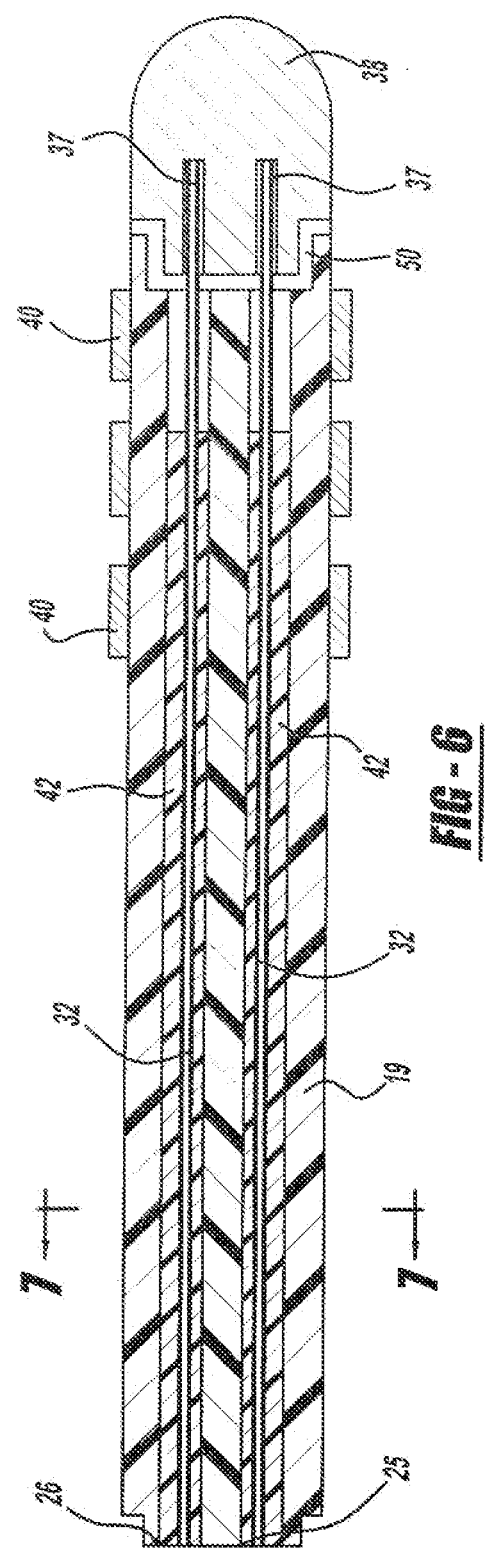
FIG. 6 is an end cross-sectional view of the tip section rotated 90 degrees from the view shown in FIG. 5.

As shown in FIGS. 4, 5 and 6, the tip section 14 comprises a short section of flexible tubing 19 having four off-axis lumens 23, 24, 25 and 26 extending therethrough. The flexible tubing 19 can comprise a single unitary piece of plastic or can comprise a series of layers, as is generally known in the art. For example, the flexible tubing 19 can comprise a plastic core, an inner plastic layer surrounding the core, a braided stainless steel mesh surrounding the inner layer, and an outer plastic layer surrounding the braided mesh. The core is preferably made by extruding the plastic over four mandrels to thereby form the four off-axis lumens 23, 24, 25 and 26, where the mandrels are removed after the core is extruded. The inner layer is formed over the core by any suitable technique, such as extrusion, which can be performed simultaneously with the extrusion of the core. Thereafter, the braided mesh is formed over the inner layer. The braided mesh comprises interwoven helical members, typically twelve, sixteen or twenty-four interwoven helical members, half extending in one direction and the other half extending in the in the counter direction. The tightness or braid angle of the helical members to a line parallel with the axis of the catheter and intersecting the helical members is not critical, but is preferably about 45. The helical members are preferably made of a conductive material having a high modulus of elasticity. Preferred helical members are made of stainless steel wire. Other methods for forming a braided mesh known in the art may be used. Finally the outer layer is formed over the braided mesh by any suitable technique, preferably extrusion.

As would be recognized by one skilled in the art, the specific number and composition of the layers of the tip section 14 is not critical. For example, the inner layer can be omitted, particularly if it is desired to have a relatively small diameter tip section. The braided mesh can also be omitted, in which case the tip section 14 can optionally comprise a unitary core formed without additional plastic layers. Preferably whatever design is used, the tip section 14 is more flexible than the catheter body 12. The outer diameter of the tip section 14, like that of the catheter body 12, is preferably no greater than about 8 french, more preferably about 6 French or less, but can vary depending on the particular application for which the catheter is to be used.

In the depicted embodiment, the off-axis lumens 23, 24, 25 and 26 are arranged in diametrically opposed pairs. Each of the diametrically opposed lumens 23 and 24 of the first pair carry an orientation sheath 54, discussed further below. The diametrically opposed lumens 25 and 26 of the second pair each carry a puller wire 32, also discussed further below. For reasons that will become apparent, the first pair of lumens 23 and 24 is preferably generally perpendicular to the second pair of lumens 25 and 26. The precise size of the lumens is not critical and will depend on the sizes of the components being carried by the lumens. As would be recognized by one skilled in the art, additional lumens could be provided if desired. For example, a central lumen could be provided for infusion of fluids.

A preferred means for attaching the catheter body 12 to the tip section 14 is illustrated in FIG. 2. The proximal end of the tip section 14 comprises an outer circumferential notch 34 that receives the inner surface of the outer wall 20 of the catheter body 12. The tip section 14 and catheter body 12 are attached by glue or the like. Before the tip section 14 and catheter body 12 are attached, however, the stiffening tube 22 is inserted into the catheter body 12. The distal end of the stiffening tube 22 is fixedly attached near the distal end of the catheter body 12 by forming a glue joint with polyurethane glue or the like. Preferably a small distance, e.g., about 3 mm, is provided between the distal end of the catheter body 12 and the distal end of the stiffening tube 22 to permit room for the catheter body 12 to receive the notch 34 of the tip section 14. A force is applied to the proximal end of the stiffening tube 22, and, while the stiffening tube 22 is under compression, a first glue joint (not shown) is made between the stiffening tube 22 and the outer wall 20 by a fast drying glue, e.g. Super Glue®. Thereafter a second glue joint is formed between the proximal ends of the stiffening tube 22 and outer wall 20 using a slower drying but stronger glue, e.g., polyurethane. Other suitable techniques for attaching the catheter body 12 and tip section 14 can also be used in accordance with the present invention.

FIG. 4 provides a schematic side cross-sectional view of the tip section 14. As shown in FIG. 4, the distal end of the tip section 14 carries a tip electrode 38. Mounted along the length of the tip section 14 are three ring electrodes 40. The length of each ring electrode 40 is not critical, but preferably ranges from about 1 mm to about 3 mm. The distance between the ring electrodes 40 is not critical so long as their edges do not touch. More or less ring electrodes 40 can be provided if desired.

The tip electrode 38 and ring electrode 40 are each connected to a separate electrode lead wire 30. Each lead wire 30 extends through a lumen 23 in the tip section 14, through the central lumen 18 in the catheter body 12 and through the control handle 16. The proximal end of each lead wire 30 extends out the proximal end of the control handle 16 and is connected to an appropriate connector, which can be plugged into or otherwise connected to a suitable monitor, source of energy, etc.

The lead wires 30 are connected to the tip electrode 38 and ring electrode 40 by any conventional technique. Connection of a lead wire 30 to the tip electrode 38 is preferably accomplished by solder or the like, as shown in FIG. 4. Connection of a lead wire 30 to a ring electrode 40 is preferably accomplished by first making a small hole through the wall of the tip section 14 into the lumen 23 through which the lead wire extends, as also shown in FIG. 4. Such a hole can be created, for example, by inserting a needle through the wall of the tip section 14 and heating the needle sufficiently to form a permanent hole. A lead wire 30 is then drawn through the hole by using a microhook or the like. The end of the lead wire 30 is then stripped of any coating and welded to the underside of the ring electrode 40, which is then slid into position over the hole and fixed in place with polyurethane glue or the like.

Two puller wires 32 extend through the catheter 10. Each puller wire 32 extends from the control handle 16, through the central lumen 18 in the catheter body 12 and into one of the off-axis lumens 25 and 26 of the tip section 14, as shown in FIG. 5. As described in more detail below, the proximal end of each puller wire 32 is anchored within the control handle 16, and the distal end of each puller wire 32 is anchored within the tip section 14.

Each puller wire 32 is made of any suitable metal, such as stainless steel or Nitinol. Preferably each puller wire 32 has a coating, such as a coating of Teflon® or the like. Each puller wire 32 has a diameter preferably ranging from about 0.006 inch to about 0.0010 inch. Preferably both of the puller wires 32 have the same diameter.

Each puller wire 32 is anchored near the distal end of the tip section 14. In the embodiment depicted in FIG. 5, the puller wires 32 are both anchored in blind holes 37 in the tip electrode 38 by a welding or the like. Alternatively, one or both puller wires 32 can be anchored to the side wall of the tip section 14, as described in U.S. patent application Ser. No. 09/710,210, filed Nov. 10, 2000, the disclosure of which is incorporated herein by reference. Other means for anchoring the puller wires 32 in the tip section 14 would be recognized by those skilled in the art and are included within the scope of the invention.

In the depicted embodiment, the distal ends of the puller wires 32 are attached to opposite sides of the tip section 14. This design permits deflection of the tip section 14 in opposing directions.

The catheter 10 further comprises two compression coils 46, each in surrounding relation to a corresponding puller wire 32, as shown in FIGS. 2 and 3. Each compression coil 46 is made of any suitable metal, such as stainless steel. Each compression coil 46 is tightly wound on itself to provide flexibility, i.e., bending, but to resist compression. The inner diameter of each compression coil 46 is slightly larger than the diameter of its associated puller wire 32. For example, when a puller wire 32 has a diameter of about 0.007 inch, the corresponding compression coil 46 preferably has an inner diameter of about 0.008 inch. The coating on the puller wires 32 allows them to slide freely within the compression coil 46. The outer surface of each compression coil 46 is covered along most of its length by a flexible, non-conductive sheath 48 to prevent contact between the compression coil 46 and the lead wires 30 within the central lumen 18. A non-conductive sheath 48 made of thin-walled polyimide tubing is presently preferred.

At the distal end of the catheter body, the two compression coils 46 are positioned in diametric opposition within the stiffening tube 22 so that they can be aligned with the two off-axis lumens 25 and 26 in the tip section 14 through which the puller wires 32 extend. The compression coils 46 and stiffening tube 22 are sized so that the compression coils 46 fit closely and slidably within the stiffening tube 22. With this design, the lead wires 30 distribute themselves around the two compression coils 46 without misaligning the coils.

The compression coils 46 are secured within the catheter body 12 with polyurethane glue or the like. Each compression coil 46 is anchored at its proximal end to the proximal end of the stiffening tube 22 in the catheter body 12 by a glue joint (not shown). When a stiffening tube 22 is not used, each compression coil is anchored directly to the outer wall 20 of the catheter body 12.

The distal end of each compression coil 46 is anchored to the distal end of the stiffening tube 22 in the catheter body 12 by a glue joint 52, or directly to the distal end of the outer wall 20 of the catheter body 12 when no stiffening tube 22 is used. Alternatively, the distal ends of the compression coils 46 may extend into the off-axis lumens 26 and 28 of the tip section 14 and are anchored at their distal ends to the proximal end of the tip section 14 by a glue joint. In the depicted embodiment, where the compression coils 46 are each surrounded by a sheath 48, care should be taken to insure that the sheath is reliably glued to the compression coil. The lead wires 30 can also be anchored in the glue joint. However, if desired, tunnels in the form of plastic tubing or the like can be provided around the lead wires at the glue joint to permit the lead wires to be slidable within the glue joint.

The glue joints preferably comprise polyurethane glue or the like. The glue may be applied by means of a syringe or the like through a hole made between the outer surface of the catheter body 20 and the central lumen 18. Such a hole may be formed, for example, by a needle or the like that punctures the outer wall 20 and the stiffening tube 22 that is heated sufficiently to form a permanent hole. The glue is then introduced through the hole to the outer surface of the compression coil 46 and wicks around the outer circumference to form a glue joint about the entire circumference of each sheath 48 surrounding each compression coil 46. Care must be taken to insure that glue does not wick over the end of the coil so that the puller wire cannot slide within the coil.

Within the off-axis lumens 25 and 26, each puller wire 32 is surrounded by a plastic sheath 42, preferably made of Teflon®. The plastic sheathes 42 prevent the puller wires 32 from cutting into the wall of the tip section 14 when the tip section is deflected. Each sheath 42 ends near the distal end of each puller wire 32. Alternatively, each puller wire 32 can be surrounded by a compression coil where the turns are expanded longitudinally, relative to the compression coils extending through the catheter body, such that the surrounding compression coil is both bendable and compressible.

Longitudinal movement of a puller wire 32 relative to the catheter body 12, which results in deflection of the tip section 14 in the direction of the side of the tip section to which that puller wire is anchored, is accomplished by suitable manipulation of the control handle 16. A suitable bidirectional control handle for use in the present invention is described in copending application Ser. No. 09/822,087, filed Mar. 30, 2001 and entitled "Steerable Catheter with a Control Handle Having a Pulley Mechanism", the disclosure of which is incorporated herein by reference. Other suitable bidirectional control handles are described in U.S. Pat. Nos. 6,123,699, 6,171,277, 6,183,463, and 6,198,974, the disclosures of which are incorporated herein by reference.

Figure 7:
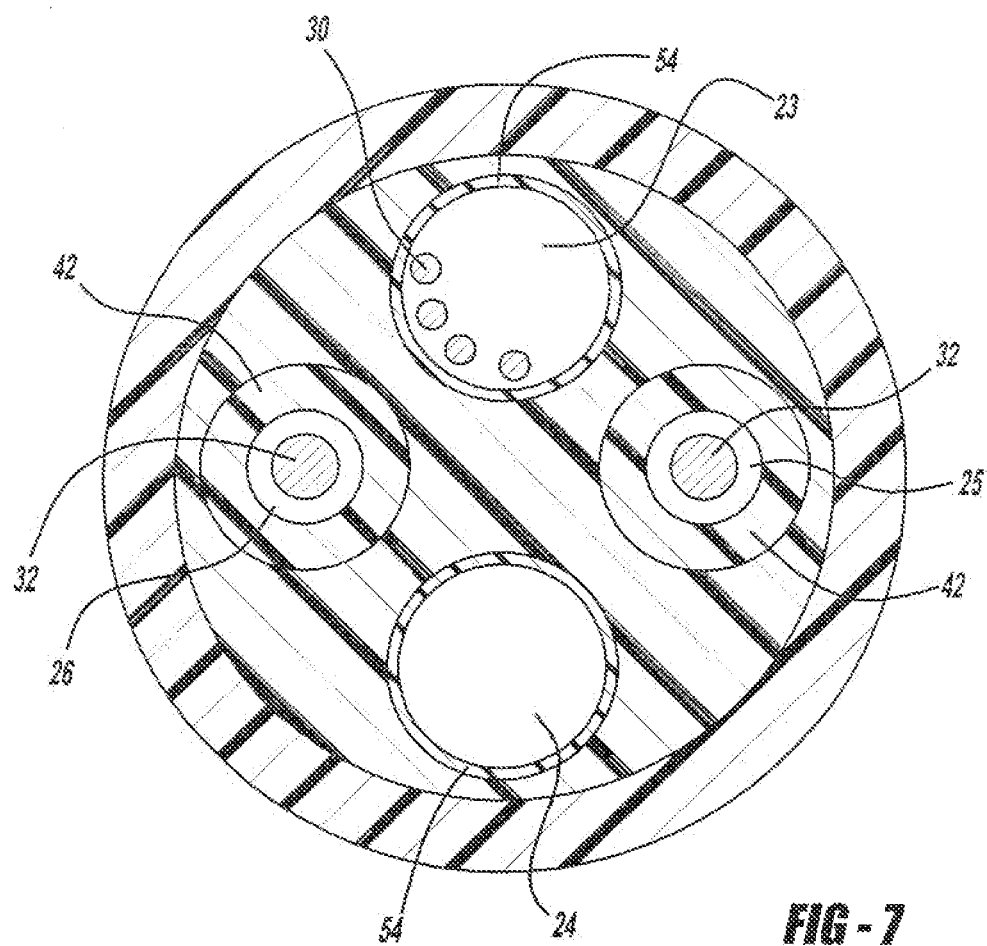
FIG. 7 is an end cross-sectional view of the tip section of FIGS. 4 and 6 taken along liens 7-7.

As illustrated in FIGS. 6 and 7, the tip section 14 includes a mechanism for enhancing control over the deflection of the tip section. The mechanism comprises two orientation sheaths 54 that extend through the two lumens 23 and 24 of the first diametrically opposed pair in the tip section 14. Each orientation sheath 54 comprises an elongated, very flexible, thin walled polymer sheath, or tube. In a preferred embodiment, the two orientation sheaths 54 are formed of thin-walled polyimide tubes which are on the order of 0.001 inches and which are inserted into the lumens and are then fed onto stainless steel mandrels. A Teflon heat shrink sleeve is then placed around the entire catheter body and heat is applied to soften the orientation sheaths and the body of the catheter while the Teflon heat shrink sleeve squeezes the materials together to bond the sheaths into the walls of the lumens.

The precise anchor point of the proximal end of each orientation sheath 54 is not critical. Preferably the proximal ends of the sheaths 54 are anchored at approximately the same longitudinal position within the catheter.

As noted above, the first pair of diametrically opposed lumens 23 and 24 extend in a plane which is generally perpendicular to the plane of the second pair of diametrically opposed lumens 25 and 26. Accordingly, the orientation sheaths 54 are provided in the plane of deflection of the tip section 14. This arrangement improves the in-plane deflection of the tip section 14 because the orientation sheaths 54 reduce the tendency of the tip section to bend in a direction other than across the plane along which the sheaths are positioned, i.e., the plane of deflection of the tip section. Such in-plane deflection increases the lateral tip stability which results in the user being able to create a greater contact force against the heart tissue.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. Accordingly, the foregoing description should not be read as pertaining only to the precise structures described and illustrated in the accompanying drawings, but rather should be read consistent with and as support to the following claims which are to have their fullest and fair scope.

What is claimed is:

1. A steerable catheter for contacting tissue comprising:
   an elongated, flexible tubular catheter body having proximal and distal ends and a lumen extending there through;
   a tip section at the distal end of the catheter body, the tip section comprising a flexible plastic tubing having first and second pairs of diametrically-opposed lumens extending there through, wherein the first pair of diametrically-opposed lumens is in a plane generally perpendicular to the plane containing the second pair of diametrically-opposed lumens, and a tip electrode;
   a control handle at the proximal end of the catheter body;
   first and second puller wires, each extending through one of the lumens of the first pair of diametrically-opposed lumens and through the lumen of the catheter body, each having a proximal end anchored to the control handle and a distal end anchored to the tip section, whereby the first puller wire is longitudinally moveable relative to the catheter body to cause deflection of the tip section in a plane in a first direction and the second puller wire is longitudinally moveable relative to the catheter body to cause deflection of the tip section in the plane in a second direction opposite the first direction;
   and first and second tubular orientation sheath members each having proximal and distal ends, each comprised of a thin walled polymide tube, each extending through one of the lumens of the second pair of diametrically opposed lumens, each having an outer diameter substantially the same as the inner diameter of the lumen through which it extends and wherein each tubular orientation sheath member is bonded along a substantial portion of the tubular orientation sheath member to the wall of one of the lumens and wherein the tubular orientation sheath members are located and configured to reduce bending of the tip section in a direction other than across the plane in which the tubular orientation sheaths are contained, thereby providing greater contact force of the tip electrode against the tissue.

2. A steerable catheter according to claim 1, wherein the tip section is more flexible than the catheter body.

3. A steerable catheter according to claim 1, wherein each tubular orientation sheath member is bonded to the respective lumen along the entire length of the tubular sheath.

4. The steerable catheter of claim 1 wherein the tubular sheath member has a wall thickness of approximately 0.001 inch.

5. The steerable catheter of claim 1 wherein each tubular orientation sheath member is bonded to the lumen using heat.

6. The steerable catheter of claim 1 wherein the proximal end of each tubular orientation sheath member is anchored at approximately the same longitudinal position within the catheter.

* * * * *